US012115172B2

United States Patent
Lin et al.

(10) Patent No.: US 12,115,172 B2
(45) Date of Patent: Oct. 15, 2024

(54) SULFATE-FREE CLEANSING COMPOSITION THAT CONFERS HIGH SALICYLIC ACID DEPOSITION

(71) Applicant: L'OREAL, Paris (FR)

(72) Inventors: Hungta Lin, Teaneck, NJ (US); Siliu Tan, Westfield, NJ (US); Ryuji Hara, Kawasaki (JP)

(73) Assignee: L'OREAL, Paris (FR)

( * ) Notice: Subject to any disclaimer, the term of this patent is extended or adjusted under 35 U.S.C. 154(b) by 81 days.

(21) Appl. No.: 17/411,903

(22) Filed: Aug. 25, 2021

(65) Prior Publication Data

US 2023/0083646 A1    Mar. 16, 2023

(51) Int. Cl.
| | |
|---|---|
| A61K 31/60 | (2006.01) |
| A61K 47/02 | (2006.01) |
| A61K 47/10 | (2017.01) |
| A61K 47/12 | (2006.01) |
| A61K 47/18 | (2017.01) |
| A61K 47/20 | (2006.01) |
| A61K 47/22 | (2006.01) |
| A61K 47/26 | (2006.01) |

(52) U.S. Cl.
CPC ............ *A61K 31/60* (2013.01); *A61K 47/02* (2013.01); *A61K 47/10* (2013.01); *A61K 47/12* (2013.01); *A61K 47/18* (2013.01); *A61K 47/183* (2013.01); *A61K 47/186* (2013.01); *A61K 47/20* (2013.01); *A61K 47/22* (2013.01); *A61K 47/26* (2013.01)

(58) Field of Classification Search
CPC ...... A61K 31/60; A61K 47/12; A61K 47/186; A61K 8/00; A61K 9/0014; A61K 47/10; A61K 47/02; A61K 47/18; A61K 47/20
See application file for complete search history.

(56) References Cited

U.S. PATENT DOCUMENTS

| | | |
|---|---|---|
| 6,436,417 B1 | 8/2002 | Singh et al. |
| 6,669,964 B2 | 12/2003 | Greenberg et al. |
| 2002/0019552 A1 * | 2/2002 | Dupont ................. C07C 303/24 558/20 |
| 2018/0353410 A1 * | 12/2018 | Kita-Tokarczyk ....... A61Q 5/02 |
| 2019/0167554 A1 | 6/2019 | Wankhade et al. |
| 2021/0128419 A1 | 5/2021 | Stebbins et al. |

FOREIGN PATENT DOCUMENTS

| | | | |
|---|---|---|---|
| CA | 2143558 A1 * | 2/1995 | ............... A61K 7/50 |
| DE | 102018215331 A1 | 3/2020 | |
| FR | 3098718 A1 | 1/2021 | |

OTHER PUBLICATIONS

Jang, Toxicol. Res. vol. 31, No. 2, pp. 105-136 (2015) (Year: 2015).*
Handbook for cleaning/decontamination of surfaces, vol. 1, 2007 (Year: 2007).*
PCT Notification of Transmittal of the International Search Report and the Written Opinion of the International Searching Authority, or the Declaration issued to counterpart application No. PCT/IB2022/057841 dated Jan. 4, 2023.
Anonymous, Mintel, "Salicylic Acid + LHA 2% Cleanser", Sep. 7, 2021, XP055947871, No. 8989590.
Anonymous, Mintel, "Clarifying Cleanser", Jul. 22, 2021, XP055947901, No. 8882779.
Anonymous, Mintel, "Nutrition & Repair Shampoo", Nov. 3, 2021, XP055947857, No. 9135378.
Search Report issued to French counterpart Application No. FR 2113194 dated Aug. 2, 2022.

* cited by examiner

*Primary Examiner* — Craig D Ricci
*Assistant Examiner* — Janet L Coppins
(74) *Attorney, Agent, or Firm* — McNees Wallace & Nurick LLC

(57) ABSTRACT

A cosmetic composition for treating acne includes at least one acne treatment active, for example, salicylic acid or a derivative thereof, which may present in an amount that is greater than 1%, by weight, based on the weight of the sulfate-free cleansing composition, and an aqueous carrier that includes at least one surfactant selected from the group consisting of sarcosinates, betaines, and combinations thereof, at least one solubilizer comprising a polyethylene glycol compound, and water. When the sulfate-free cleansing composition is applied to a keratinous tissue it demonstrates deposition and retention of the beta hydroxy acid on the keratinous tissue after rinsing with water.

20 Claims, No Drawings

SULFATE-FREE CLEANSING COMPOSITION THAT CONFERS HIGH SALICYLIC ACID DEPOSITION

FIELD OF THE INVENTION

The present disclosure is directed to a skin care composition, in particular, a cosmetic cleansing composition for addressing acne with high efficacy to deliver and deposit actives to skin, particularly salicylic acid and derivatives thereof.

BACKGROUND OF THE INVENTION

Acne is a common skin disorder and is treated using a variety of different agents. Salicylic acid, a mild beta-hydroxy acid, known for facilitating sloughing of dead skin cells and other cellular debris, is often used in treating acne, as well as other skin conditions that include psoriasis, keratoses, and ichthyoses. Commercial forms of cosmetic products that include salicylic acid include peels, cleansers, and leave on treatment in the forms of lotions, creams, and make ups. A challenge with many of these product forms is that they deliver salicylic acid that is only transiently available on the skin, such as in cleansers and peels, or that is in relatively low amounts, thus precluding sustained effectiveness on the skin for addressing acne and other skin conditions that benefit from the agent. A further challenge with these products is the requirement of irritating sulfates to solubilize salicylic acid in amounts of 1% or more, by weight. Without sulfates, salicylic acid is vulnerable to precipitation, affecting not only the availability of the active for treatment, but also adversely affecting the stability of the product.

Accordingly, there is a need for a composition that overcomes the shortcomings of the prior art and provides benefits that include the ability to cleanse skin and provide persistent delivery of a skin active, for example, salicylic acid and derivatives thereof, after cleansing to enhance the treatment of skin with acne or that is prone to acne. The present invention provides such a composition.

BRIEF SUMMARY OF THE INVENTION

In accordance with the various embodiments, a cosmetic composition is provided for cleansing the skin in a rinse-off formulation that provides a stable disposition of an acne treatment active, for example, beta hydroxy acid, on the skin that is resistant to removal by rinsing with or without use of a cleansing apparatus, such as a cleansing brush. In the various embodiments, the inventive composition includes at least one acne treatment active, for example, salicylic acid or a derivative thereof, which may present in an amount that is greater than 1%, by weight, based on the weight of the sulfate-free cleansing composition, and an aqueous carrier that includes at least one surfactant selected from the group consisting of sarcosinates, betaines, and combinations thereof, at least one solubilizer comprising a polyethylene glycol compound, and water. The retention of acne treatment active on the skin even beyond cleansing effectively extends the duration of the acne treatment active availability on the skin for addressing acne and other skin conditions that are responsive to acne treatment actives, in particular, salicylic acid and other beta hydroxy acids and derivatives thereof, thereby providing sustained treatment in an otherwise rinsible formulation. In some embodiments, the composition is formulated as a cleanser.

In some embodiments, the disclosure provides a sulfate-free cleansing composition that includes at least one acne treatment active, for example, at least one beta hydroxy acid. In some embodiments, the at least one beta hydroxy acid is selected from the group consisting of -n-octanoylsalicylic acid, salicylate, sodium salicylate, salicylic acid, willow extract, beta hydroxybutanoic acid, tropic acid, and trethocanic acid, and combinations thereof. In some embodiments, the at least one beta hydroxy acid comprises salicylic acid or a derivative thereof. In some embodiments, the at least one beta hydroxy acid is present in an amount that is greater than 1%, by weight, based on the weight of the sulfate-free cleansing composition. The sulfate-free cleansing composition also includes an aqueous carrier that includes at least one surfactant selected from the group consisting of sarcosinates, betaines, and combinations thereof. In some embodiments, the at least one surfactant includes one, two, three or more surfactants selected from the group consisting of sarcosinates, betaines, and combinations thereof, present in a total amount that is not greater than about 50%, by weight, based on the weight of the sulfate-free cleansing composition. The aqueous carrier also includes at least one solubilizer comprising a polyethylene glycol compound; and water.

In some embodiments, the sulfate-free cleansing composition may include one or more additional surfactants in addition to the total amount of surfactants selected from the group consisting of sarcosinates, betaines, and combinations thereof. In some embodiments, the sulfate-free cleansing composition expressly excludes sulfate-based and/or sulfate-containing surfactants. In some embodiments, the at least one surfactant has an HLB that is equal to or greater than 25.

In some embodiments, salicylic acid is present in an amount that is in a range from greater than 1% to about 4%, by weight, based on the weight of the sulfate-free cleansing composition. In some embodiments, salicylic acid is present in an amount that is in a range from greater than 1.2% to about 2%, by weight, based on the weight of the sulfate-free cleansing composition.

In some embodiments, the at least one surfactant is present in an amount that is in a range from about 0.2% to about 50%, by weight, based on the weight of the sulfate-free cleansing composition. In some embodiments, the at least one surfactant comprises a blend of two or more surfactants, each present in an amount that is in a range from about 5% to about 25%, by weight, based on the weight of the sulfate-free cleansing composition.

In some embodiments, the at least one solubilizer comprising a polyethylene glycol compound is present in an amount that is in a range from about 0.2% to about 5%, by weight, based on the weight of the sulfate-free cleansing composition.

In some embodiments, the at least one surfactant comprises one of sodium laureth sulfosuccinate (and) sodium lauryl sulfoacetate, sodium Lauroyl Sarcosinate or a combination thereof. More generally, in some embodiments, the at least one surfactant is selected from the group consisting of sodium laureth sulfosuccinate (and) sodium lauryl sulfoacetate, sodium Lauroyl Sarcosinate, Disodium Laureth Sulfosuccinate, Disodium Lauryl Sulfosuccinate, Diethylhexyl Sodium Sulfosuccinate, Disodium Laureth Sulfosuccinate, Sodium Lauryl Sulfoacetate (and) Disodium Laureth Sulfosuccinate, Sodium Lauryl Sulfoacetate, Cocamidopropyl Betaine, Lauryl Betaine (and) Cetyl Betaine, Coco-Betaine, Sodium Lauroyl Sarcosinate, Sodium Cocoyl Sarcosinate, Isopropyl Lauroyl Sarcosinate, and combinations thereof.

In some embodiments, the at least one solubilizer comprising a polyethylene glycol compound comprises PEG-7 glyceryl cocoate, PEG-60 hydrogenated castor oil, PEG-150 pentaerythrityl tetrastearate, or combinations thereof. More generally, in some embodiments, the at least one solubilizer comprising a polyethylene glycol is selected from the group consisting of PEG-7 glyceryl cocoate, PEG-60 hydrogenated castor oil, PEG-150 pentaerythrityl tetrastearate, PEG-40 Hydrogenated Castor Oil, PEG-80 Hydrogenated Castor Oil, PEG-30 Glyceryl Cocoate, PEG-80 Glyceryl Cocoate, and combinations thereof.

In some embodiments, the sulfate-free cleansing composition, when applied to a keratinous tissue, demonstrates deposition and retention of the beta hydroxy acid on the keratinous tissue after rinsing with water.

In some embodiments, the sulfate-free cleansing composition exhibits high foaming and demonstrates stability from phase separation and remains free from hazing at an ambient temperature of about 45° C. for a period of at least 2 months.

In some embodiments, the sulfate-free cleansing composition is free of cationic compounds, sulfate-based surfactants, or any combination thereof.

In some embodiments, the sulfate-free cleansing composition is free of sulfate containing compounds, in particular, but not limited to sodium lauryl sulfate, Sodium Lauryl Sulfate, Sodium laureth sulfate, sodium lauryl ether sulfate, Ammonium lauryl sulfate, Ammonium Laureth Sulfate, or any combinations of these.

In some embodiments, the sulfate-free cleansing composition further comprises one or more additives selected from the group consisting of water-based solvents, humectants, pH adjusters, chelating agents, skin care actives, preservatives, fillers, fragrances, dyes, pigments, and combinations thereof.

In some embodiments, the sulfate-free cleansing composition further comprises one or more additives selected from the group consisting of allantoin, potassium hydroxide, dyes, pigments, dipropylene glycol, panthenol, phenoxyethanol, menthol, tocopheryl acetate, glycerin, lactic acid, fragrance, zinc PCA, tetrasodium glutamate diacetate, sorbitol, cetylpyridinium chloride, and combinations thereof.

In some embodiments, the disclosure provides a sulfate-free cleansing composition that includes at least one acne treatment active comprising at least one beta hydroxy acid that comprises salicylic acid or a derivative thereof, present in an amount in a range from greater than 1% up to and including about 3%, by weight, based on the weight of the sulfate-free cleansing composition; and an aqueous carrier that includes a blend of surfactants selected from the group consisting of sarcosinates, betaines, and combinations thereof, each one of the at least one surfactant present in a range from about 0.2% to about 25%, the total amount of the blend of surfactants not greater than about 50%, all amounts by weight, based on the weight of the sulfate-free cleansing composition, wherein each surfactant in the blend of surfactants has an HLB that is greater than about 25; and at least one solubilizer comprising a polyethylene glycol compound present in an amount that is in a range from about 0.2% to about 5%, by weight, based on the weight of the sulfate-free cleansing composition; and iii. water.

In some embodiments, the at least one surfactant comprises one of sodium laureth sulfosuccinate (and) sodium lauryl sulfoacetate, sodium Lauroyl Sarcosinate, or a combination thereof, and is more generally selected from the group consisting of sodium laureth sulfosuccinate (and) sodium lauryl sulfoacetate, sodium Lauroyl Sarcosinate, Disodium Laureth Sulfosuccinate, Disodium Lauryl Sulfosuccinate, Diethylhexyl Sodium Sulfosuccinate, Disodium Laureth Sulfosuccinate, Sodium Lauryl Sulfoacetate (and) Disodium Laureth Sulfosuccinate, Sodium Lauryl Sulfoacetate, Cocamidopropyl Betaine, Lauryl Betaine (and) Cetyl Betaine, Coco-Betaine, Sodium Lauroyl Sarcosinate, Sodium Cocoyl Sarcosinate, Isopropyl Lauroyl Sarcosinate, and combinations thereof; and wherein the at least one solubilizer comprising a polyethylene glycol compound comprises PEG-7 glyceryl cocoate, PEG-60 Hydrogenated castor oil, PEG-150 pentaerythrityl tetrastearate, or combinations thereof, and is more generally selected from the group consisting of PEG-7 glyceryl cocoate, PEG-60 hydrogenated castor oil, PEG-150 pentaerythrityl tetrastearate, PEG-40 Hydrogenated Castor Oil, PEG-80 Hydrogenated Castor Oil, PEG-30 Glyceryl Cocoate, PEG-80 Glyceryl Cocoate, and combinations thereof, and the sulfate-free cleansing composition optionally further comprising one or more additives selected from the group consisting of water-based solvents, humectants, pH adjusters, chelating agents, skin care actives, preservatives, fillers, fragrances, dyes, pigments, and combinations thereof.

In some embodiments, the sulfate-free cleansing composition exhibits high foaming and demonstrates stability from phase separation and remains free from hazing at an ambient temperature of about 45° C. for a period of at least 2 months, and wherein the sulfate-free cleansing composition is free of cationic compounds.

In some embodiments, the sulfate-free cleansing composition, when applied to a keratinous tissue, demonstrates deposition and retention of the beta hydroxy acid on the keratinous tissue after rinsing with water.

In some embodiments, the disclosure provides a sulfate-free cleansing composition that includes at least one acne treatment active comprising at least one beta hydroxy acid that comprises salicylic acid or a derivative thereof, present in an amount that is in a range from greater than 1% to about 3%, or from about 1.2% to about 2%, by weight, based on the weight of the sulfate-free cleansing composition; and an aqueous carrier that includes a blend of surfactants selected from the group consisting of sarcosinates, betaines, and combinations thereof, the blend of surfactants comprising sodium laureth sulfosuccinate (and) sodium lauryl sulfoacetate present in an amount that is about 10%, sodium lauroyl sarcosinate present in an amount that is about 10%, and cocamidopropyl betaine present in an amount that is about 6%, all amounts by weight, based on the weight of the sulfate-free cleansing composition, at least one solubilizer comprising a polyethylene glycol compound, the at least one solubilizer comprising PEG-7 glyceryl cocoate; water; and optionally, one or more additives selected from the group consisting of water-based solvents, humectants, pH adjusters, chelating agents, skin care actives, preservatives, fillers, fragrances, dyes, pigments, and combinations thereof, wherein the sulfate-free cleansing composition, when applied to a keratinous tissue, demonstrates deposition and retention of the beta hydroxy acid on the keratinous tissue after rinsing with water.

The sulfate-free cleansing composition, when applied to a keratinous tissue, demonstrates deposition and retention of the beta hydroxy acid on the keratinous tissue after rinsing with water, wherein the deposition and enhanced salicylic acid retention may be demonstrated by measurement of color change resulting from complex formation between the acid and a metal salt, such as $FeCl_3$.

In various embodiments, the disclosure provides a method for delivering to skin a cleansing composition capable of depositing salicylic acid for persistent retention on the skin after rinsing with water; and, wherein the sulfate-free cleansing composition is applied to skin that is prone to acne, followed by washing or scrubbing, optionally with a provided brush or other applicator, followed by rinsing.

Use of the inventive cosmetic cleansing composition for treatment of skin conditions such as acne is characterized by deposition and retention on the skin after rinsing of the beta hydroxy acid, for example, salicylic acid, wherein the deposition and enhanced salicylic acid retention may be demonstrated by measurement of color change resulting from complex formation between the acid and a metal salt, such as $FeCl_3$.

It is to be understood that both the foregoing general description and the following detailed description are exemplary and explanatory only and are not restrictive of the invention.

DETAILED DESCRIPTION OF THE INVENTION

The term "cleanser" as used herein can be any cosmetic composition utilized for application to a keratinous tissue for cleansing the skin, removal of make-up and the like.

The terms "essentially free of sulfate," "essentially free of sulfate-based surfactant," "essentially free of sulfate-based surfactant," and "essentially sulfate-free" refer to the essential absence of sulfate contents in the sulfate-free cleansing composition of the present invention. In reference to some embodiments, the term "sulfate-free" means that sulfate has not been added as a component. In reference to some embodiments, the sulfate-free cleansing composition is devoid of sulfate. In reference to some embodiments, the sulfate-free cleansing composition is free or devoid of sulfates that may include, but are not limited to, anionic alkyl sulfates and alkyl ether sulfates. In reference to some embodiments, while it is preferred that no sulfate-based surfactants are present in the sulfate-free cleansing composition, it is possible to have very small amounts of sulfate-based surfactants in the sulfate-free cleansing composition of the invention, provided that these amounts do not materially affect the advantageous properties of the sulfate-free cleansing composition, in particular with respect to mildness to skin. Thus, a sulfate-based surfactant can be present in the sulfate-free cleansing composition at an amount of less than about 0.2% by weight, or less than about 0.1% by weight, or less than about 0.05% by weight, or about 0% by weight, based on the total weight of the sulfate-free cleansing composition.

The term "free from hazing" as used herein means that the test formulations are essentially 100% clear, likely representing that essentially all of the salicylic acid is maintained as solubilized, clarity, or free from haze, being confirmed visually and a spectrophotometer or similar instrument to measure the type and amount of the light that passes through wherein 100% of Light Transmission (using, for example, a Varian Cary 5000 uv-vis-nir spectrophotometer) is equivalent to =100% clear and free from haze.

The term "high foaming" as used herein means the absolute or relative height of a formulation after agitation and measurement of generated foam height using an analyzer (for example Kruss DFA100 Dynamic Foam Analyzer).

The term "skin" as used herein includes skin materials containing keratin such as facial and body skin, scalp, eyebrows, and lips. As referenced in the examples herein, Bioskin is a pseudo skin manufactured substrate that is a substitute for skin and is known in the cosmetics and other industries for its representative similarity to keratinous substrates, such as skin.

The term "stable disposition of an acne treatment active" as used herein means deposition, for example, beta hydroxy acid, on the skin that is resistant to removal by rinsing and/or use of a cleansing apparatus, such as a cleansing brush.

The term "stability" as used herein means that the sulfate-free cleansing composition does not demonstrate phase separation and remains free from hazing at an ambient temperature of about 45° C. for a period of at least 2 months.

The sulfate-free cleansing composition, can comprise, consist of, or consist essentially of the essential elements and limitations of the invention described herein, as well as any additional or optional ingredients, components, or limitations described herein or otherwise useful.

The sulfate-free cleansing composition may be formulated as a cleanser, as described herein, for cleansing the skin in a rinse-off formulation that provides a stable disposition of an acne treatment active, for example, beta hydroxy acid, on the skin that is resistant to removal by rinsing and/or use of a cleansing apparatus, such as a cleansing brush. The retention of salicylic acid on the skin even beyond cleansing with or without a cleansing brush effectively extends the duration of the salicylic acid availability on the skin for addressing acne and other skin conditions that are responsive to salicylic acid and other beta hydroxy acids, thereby providing sustained treatment in an otherwise rinsible formulation. In some embodiments the acne treatment active is salicylic acid.

The sulfate-free cleansing composition overcomes shortcomings in the art pertinent to salicylic acid induced instability in cosmetic compositions. Unexpectedly, employing various embodiments of the sulfate-free cleansing composition as disclosed and as exemplified herein, the sulfate-free cleansing composition demonstrates deposition and retention of beta hydroxy acid, after rinsing, that may be shown by measurement of color change resulting from complex formation between the acid and a metal salt, such as $FeCl_3$.

The deposition and enhanced salicylic acid retention was demonstrated herein in the in vitro tests by measurement of color change resulting from complex formation between the acid and a metal salt, such as $FeCl_3$. As shown in the examples, the sulfate-free cleansing composition, when applied to a keratinous tissue type material demonstrates deposition and retention of the beta hydroxy acid on the keratinous tissue after rinsing with water, wherein the deposition and enhanced salicylic acid retention may be demonstrated by measurement of color change resulting from complex formation between the acid and a metal salt, such as $FeCl_3$. In vitro tests reported herein have confirmed deposition of salicylic acid on a pseudo skin material, and retention after rinsing, for example, through at least a first rinsing of about 30 seconds and removal of the sulfate-free cleansing composition using a brush apparatus.

In addition, the inventive sulfate-free cleansing composition demonstrates stability from phase separation, high foaming quality, high transparency (free from hazing) and a mild aesthetic when applied to skin.

Cosmetic Composition

In accordance with the various embodiments, the sulfate-free cleansing composition is suitable for application to keratinous tissue for cleansing, particularly for addressing acne. In some embodiments, the sulfate-free cleansing composition is free of, or substantially free of, or devoid of one or more of sulfates, including but not limited to sulfate-based or sulfate-containing surfactants, and cationic compounds.

In some embodiments, the disclosure provides a sulfate-free cleansing composition that includes at least one acne treatment active, for example, at least one beta hydroxy acid. In some embodiments, the at least one beta hydroxy acid is selected from the group consisting of -n-octanoylsalicylic acid, salicylate, sodium salicylate, salicylic acid, willow extract, beta hydroxybutanoic acid, tropic acid, and trethocanic acid, and combinations thereof. In some embodiments, the at least one beta hydroxy acid comprises salicylic acid or a derivative thereof. In some embodiments, the at least one beta hydroxy acid is present in an amount that is greater than 1%, by weight, based on the weight of the sulfate-free cleansing composition. The sulfate-free cleansing composition also includes an aqueous carrier that includes at least one surfactant selected from the group consisting of sarcosinates, betaines, and combinations thereof. In some embodiments, the at least one surfactant includes one, two, three or more surfactants selected from the group consisting of sarcosinates, betaines, and combinations thereof. In some embodiments, the at least one surfactant or blend of surfactants is present in a total amount that is not greater than about 50%, by weight, based on the weight of the sulfate-free cleansing composition. The aqueous carrier also includes at least one solubilizer comprising a polyethylene glycol compound and water. In some embodiments, the at least one surfactant has a high HLB that is at least equal to or greater than 25.

Beta Hydroxy Acid

In accordance with the various embodiments, the sulfate-free cleansing composition comprises at least one acne treatment active comprising beta hydroxy acid. In some embodiments, the sulfate-free cleansing composition includes a beta hydroxy acid comprising salicylic acid.

In some particular embodiments according to the disclosure, the sulfate-free cleansing composition includes salicylic acid present in the sulfate-free cleansing composition in an amount that ranges from about 0.2% to about 2% by weight, based on the total weight of the sulfate-free cleansing composition.

The term "beta-hydroxy acid" is understood to mean, according to the present invention, a carboxylic acid having a hydroxyl functional group and a carboxylic functional group separated by two carbon atoms. A beta hydroxy acid can be present in the sulfate-free cleansing composition in the form of the free acid and/or in the form of one of its associated salts (salts with an organic base or an alkali metal, in particular), especially according to the final pH imposed on the sulfate-free cleansing composition.

The beta hydroxy acid is selected from one or more of salicylic acid and derivatives thereof (including 5-n-octanoylsalicylic acid, salicylate, sodium salicylate, and willow extract), capryloyl salicylic acid, beta hydroxybutanoic acid, tropic acid, and trethocanic acid.

The total amount of beta hydroxy acid includes, in some particular embodiments, from about 0.1% up to and not more than about 2% of beta hydroxy acid, by weight, based on the total weight of the sulfate-free cleansing composition. In some embodiments, the sulfate-free cleansing composition includes and up to and not more than about 2%, or about 1.9% of beta hydroxy acid. In some embodiments, the sulfate-free cleansing composition includes from about 0.1% to about 1% of beta hydroxy acid. In some embodiments, the sulfate-free cleansing composition includes and up to and not more than about 1% of beta hydroxy acid. In some embodiments, the sulfate-free cleansing composition includes more than about 2% beta hydroxy acid.

In accordance with the various embodiments, the amount of beta-hydroxy acid present in the sulfate-free cleansing composition is in the range from about 0.1% to about 2%, and in some embodiments from about 0.1% to about 1.5%, and in some embodiments from about 0.1% to about 1%, including increments and all ranges and subranges therein and there between, by weight, based on the total weight of the sulfate-free cleansing composition. One of ordinary skill in the art, however, will appreciate that other ranges are within the scope of the invention.

Thus, the at least one beta hydroxy acid is present in the sulfate-free cleansing composition from about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, to about 2.0 weight percent, including increments and all ranges and subranges therein and there between.

In some embodiments, the sulfate-free cleansing composition is free or essentially free from any cationic agent, for example, cationic polymers, including, but not limited to nature-based polymers that are polysaccharides, other natural (i.e., plant, animal, or bacterial based), synthetic, or modified cationic nature-based or synthetic polymers. In some embodiments, the sulfate-free cleansing composition is free or essentially free of cationic polymers selected from chitosan, chitosan derivatives, chitin, starch, starch derivatives, cellulose (ethylcellulose, nitrocellulose, hemicellulose, and hemicellulose derivatives), alginates, mannans, xylans, lignins, arabans, galacturonans, alginate-based compounds, chitin, glucuronoxylans, arabinoxylans, xyloglucans, glucomannans, fructosans such as inulin, pectic acids and pectins, arabinogalactans, agars, glycosaminoglycans, gum arabics, tragacanth gums, ghatti gums, karaya gums, locust bean gums, xanthan gums, mucopolysaccharides, chondroitin sulfates, polyquaterniums, for example, polyquaternium-47 (1-Propanaminium, N,N,N-trimethyl-3-[(2-methyl-1-oxo-2-propenyl)amino]-chloride, polymer with methyl 2-propenoate and 2-propenoic acid, cationic acrylic polymers, polyacrylates, for example, polyacrylate-1, polyacrylate-2, polyacrylate-3, polyacrylate-4, polyacrylate-16, polyacrylate-17, polyacrylate-18, polyacrylate-19, polyacrylate-21, and any combination of these.

Surfactant

In accordance with the various embodiments, the sulfate-free cleansing composition comprises at least one high HLB surfactant selected from the group consisting of sarcosinates, betaines, and combinations thereof. In some embodiments, the sulfate-free cleansing composition comprises more than one high HLB surfactant, for example, two or more high HLB surfactants, wherein each such high HLB surfactant has an HLB that is equal to or greater than 25 (i.e., the surfactant it highly hydrophilic).

The term "Hydrophilic-Lipophilic Balance" or "HLB," refers to an empirical expression for the relationship of the hydrophilic and hydrophobic groups of an emulsifier. This term is well known to those skilled in the art. See, e.g., "The HLB system. A time-saving guide to Emulsifier Selection" (Pub: ICI Americas Inc., 1984) and US2006/0217283 at [0053].

In various embodiments, the sulfate-free cleansing composition comprises at least one high HLB surfactant has an HLB that is =/>25, for example the at least one surfactant has an HLB that is in a range from about 25, 26, 27, 28, to about 40 or more, including increments of about 0.1 therein and therebetween.

In some embodiments, the at least one surfactant selected from the group consisting of sarcosinates, betaines, and combinations thereof comprises one of sodium laureth sulfosuccinate (and) sodium lauryl sulfoacetate, sodium Lauroyl Sarcosinate [list others], or a combination thereof. In some embodiments, the at least one surfactant selected from the group consisting of sarcosinates, betaines, and combinations thereof includes the combination of surfactants that comprise comprises sodium laureth sulfosuccinate (and) sodium lauryl sulfoacetate, and sodium lauroyl sarcosinate.

More generally, in some embodiments, the at least one surfactant is selected from the group consisting of sodium laureth sulfosuccinate (and) sodium lauryl sulfoacetate, sodium Lauroyl Sarcosinate, Disodium Laureth Sulfosuccinate, Disodium Lauryl Sulfosuccinate, Diethylhexyl Sodium Sulfosuccinate, Disodium Laureth Sulfosuccinate, Sodium Lauryl Sulfoacetate (and) Disodium Laureth Sulfosuccinate, Sodium Lauryl Sulfoacetate, Cocamidopropyl Betaine, Lauryl Betaine (and) Cetyl Betaine, Coco-Betaine, Sodium Lauroyl Sarcosinate, Sodium Cocoyl Sarcosinate, Isopropyl Lauroyl Sarcosinate, and combinations thereof.

In some embodiments, the at least one surfactant is present in an amount that is in a range from about 0.2% to about 50%, by weight, based on the weight of the sulfate-free cleansing composition. In some embodiments, the at least one surfactant comprises a blend of two or more surfactants, each present in an amount that is in a range from about 5% to about 25%, by weight, based on the weight of the sulfate-free cleansing composition.

In various embodiments, each of the at least one surfactant may be present in an amount in the range of from about 0.2% to about 50%, and the total amount of surfactant may be present in a range from about 0.2% to about 50%. In some embodiments, each of the at least one surfactant is present in an amount that is at least 0.2%, or about 1%, or about 5%, or about 6%, or about 10%, or about 15%, to about 20%, or up to about 50%, or about 0.1% to about 5%, or to about 3% or to about 6%, or about 5% to about 10%, or about 10% to about 15%, or about 10% to about 30%, or about 30% to about 50%, or any value, range, or sub-range therebetween by weight, based on the weight of the composition.

Thus, in various embodiments, each of the at least one surfactant or combination of surfactants may be present in a composition according to the disclosure from 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 120, 21, 22, 23, 24, 25, 26, 27, 28, 29, 30, 3, 32, 33, 34, 35, 36, 37, 38, 39, 40, 41, 42, 43, 44, 45, 46, 47, 48, 49 to about 50 percent, including increments and ranges therein and there between.

In some embodiments, the sulfate-free cleansing composition may include other surfactants in addition to the at least one surfactant selected from the group consisting of sarcosinates, betaines, and combinations thereof, and such other surfactants may be present in amounts that exceed the total amount of at least one surfactant selected from the group consisting of sarcosinates, betaines, and combinations thereof. That is to say, the at least one surfactant selected from the group consisting of sarcosinates, betaines, and combinations thereof may be present in a total amount that is not greater than about 50%, and any additional surfactants may be present in amounts that are in addition to that among. In other embodiments, the total amount of all surfactants that may be present in the sulfate-free cleansing composition are not more than a total amount that is not greater than 50%, by weight, of the total sulfate-free cleansing composition.

Solubilizer

In accordance with the various embodiments, the sulfate-free cleansing composition comprises at least one solubilizer comprising a polyethylene glycol compound.

In some embodiments, the at least one solubilizer comprising a polyethylene glycol compound is selected from the group consisting of PEG-7 glyceryl cocoate, PEG-60 hydrogenated castor oil, PEG-150 pentaerythrityl tetrastearate [list others], or combinations thereof. In some embodiments, the at least one solubilizer comprising a polyethylene glycol includes at least one or a combination of PEG-7 glyceryl cocoate, PEG-60 hydrogenated castor oil, and PEG-150 pentaerythrityl tetrastearate.

More generally, in some embodiments, the at least one solubilizer comprising a polyethylene glycol is selected from the group consisting of PEG-7 glyceryl cocoate, PEG-60 hydrogenated castor oil, PEG-150 pentaerythrityl tetrastearate, PEG-40 Hydrogenated Castor Oil, PEG-80 Hydrogenated Castor Oil, PEG-30 Glyceryl Cocoate, PEG-80 Glyceryl Cocoate, and combinations thereof.

In some embodiments, the at least one solubilizer is present in an amount that is in a range from about 0.2% to about 5%, by weight, based on the weight of the sulfate-free cleansing composition. In some embodiments, the at least one solubilizer comprises a blend of two or more solubilizer comprising a polyethylene glycol compound, each present in an amount that is in a range from about 0.2% to about 5%, by weight, based on the weight of the sulfate-free cleansing composition.

In various embodiments, each of the at least one solubilizer comprising a polyethylene glycol compound may be present in an amount in the range of from about 0.2% to about 5%, and the total amount of solubilizer may be present in a range from about 0.2% to about 10%. In some embodiments, each of the at least one solubilizer is present in an amount that is at least 0.2%, or about 0.5%, or about 0.75%, or about 1%, or about 5%, or about 10%, to about 1%, or up to about 10%, or about 0.1% to about 5%, or to about 0.2% or to about 3%, or about 0.75% to about 1%, or any value, range, or sub-range therebetween by weight, based on the weight of the sulfate-free cleansing composition.

Thus, in various embodiments, each of the at least one surfactant or combination of surfactants may be present in a composition according to the disclosure from 0.2, 0.3, 0.4, 0.5, 0.6, 0.7, 0.8, 0.9, 1, 2, 3, 4, 5, 6, 7, 8, 9, to about 10 percent, including increments and ranges therein and there between.

Water

In accordance with the various embodiments, the sulfate-free cleansing composition includes water.

In various embodiments, the sulfate-free cleansing composition comprises from about 5% to about 90% water, and in some embodiments from about 20% to about 85% water, and in some embodiments from about 50% to about 85% water, and in some embodiments from about 60% to about 80% water, and in some embodiments from about 65% to about 75%, water, including increments and all ranges and subranges therein and there between, by weight, based on the total weight of the sulfate-free cleansing composition. One of ordinary skill in the art, however, will appreciate that other ranges are within the scope of the invention. Thus, water is present, by weight, based on the total weight of the sulfate-free cleansing composition, from about 5, 10, 15, 20, 25, 30, 35, 40, 45, 50, 55, 60, 65, 66, 67, 68, 69, 70, 71, 72, 73, 74, 75, 80, 85, to about 90 weight percent, including increments and all ranges and subranges therein and there between.

The water used in the sulfate-free cleansing composition may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Optional Additives

In some embodiments, the sulfate-free cleansing composition further comprises one or more additives selected from the group consisting of water-based solvents, humectants, pH adjusters, chelating agents, skin care actives, preservatives, fillers, fragrances, dyes, pigments, and combinations thereof.

In some particular embodiments, the sulfate-free cleansing composition further comprises one or more additives selected from the group consisting of allantoin, potassium hydroxide, dyes, pigments, dipropylene glycol, panthenol, phenoxyethanol, menthol, tocopheryl acetate, glycerin, lactic acid, fragrance, zinc PCA, tetrasodium glutamate diacetate, sorbitol, cetylpyridinium chloride, and combinations thereof.

In some embodiments, the sulfate-free cleansing composition includes one or more of other optional ingredients selected from the group consisting of skin care actives, humectants, conditioning agents, thickeners, viscosity adjusters, cooling agents, fillers, antimicrobials, preservatives, pH adjusters, chelating agents, and combinations thereof.

In some embodiments, a cleansing composition includes at least one additive used in the cosmetics field which does not affect the properties of the sulfate-free cleansing composition according to the invention, such as, fragrances, pH adjusters (citric acid, sodium chloride, lactic acid); neutralizing or pH-adjusting agents (e.g., triethylamine (TEA) and sodium hydroxide, Trisodium ethylenediamine disuccinate, and combinations thereof), other cosmetically acceptable additives, such as but not limited to, pearlescent agents, silica, and coloring materials; essential oils; fruit extracts, for example, Pyrus Malus (Apple) Fruit Extract, and Aloe Barbadensis Leaf Juice Powder; conditioning agents such as C12-15 Alkyl lactate and C12-15 Alcohols; Thickeners, for example Ammonium polyacryloyldimethyl taurate, Propylene glycol and PEG-55 propylene glycol oleate; viscosity adjusters, for example, Sodium chloride and Hexylene Glycol; cooling agents such as menthol; fillers, for example Kaolin; or any combination thereof. Although the optional additives are given as examples, it will be appreciated that other optional components compatible with cosmetic applications known in the art may be used.

In some embodiments, the sulfate-free cleansing composition includes a blend of humectants, antimicrobials, preservatives, actives, pH adjusters and chelating agents comprising C12-15 Alkyl lactate and C12-15 Alcohols, citric acid, trisodium ethylenediamine disuccinate, phenoxyethanol, caprylyl glycol, chlorphenesin, ammonium polyacryloyldimethyl taurate, propylene glycol and peg-55 propylene glycol oleate, and kaolin.

In accordance with the various embodiments, the amount of one or more additives, alone or in combination, present in the sulfate-free cleansing composition can be present in the sulfate-free cleansing composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the sulfate-free cleansing composition. One of ordinary skill in the art, however, will appreciate that other ranges are within the scope of the invention.

Thus, any one or a combination of additives may be present, by weight, based on the total weight of the sulfate-free cleansing composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Although the optional additives are given as examples, it will be appreciated that other optional components compatible with cosmetic applications known in the art may be used that are suitable. It will be appreciated by a skilled artisan that any optional additives are present only to the extent and in amounts that do not materially adversely affect the basic and novel characteristic(s) of the claimed disclosure. Thus, in some embodiments that include optional additives, such optional additives will not materially adversely affect the sulfate-free cleansing composition.

More generally, it will be appreciated by a skilled artisan that any solvents, humectants, preservatives, or other additives are present only to the extent and in amounts that do not materially adversely affect the basic and novel characteristic(s) of the claimed invention.

Water-Soluble Solvents

In accordance with some embodiments, the cleansing composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), polyols, glycols, and combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and combinations thereof.

In accordance with the various embodiments total amount of the at least one water-soluble solvent, when present, may vary, is from about 0.5% to about 25%, or from about 0.5% to about 20%, or from about 1% to about 20%, or from about 1% to about 10%, or from about 2% to about 5% or any suitable combination, sub-combination, range, or sub-range thereof by weight, based on the weight of the sulfate-free cleansing composition. One of ordinary skill in the art, however, will appreciate that other ranges are within the scope of the invention.

Thus, any one water-soluble solvent, when present, is present, by weight, based on the total weight of the sulfate-free cleansing composition, from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Humectant

In accordance with the disclosure, one or more humectants may be present in the sulfate-free cleansing composition. In some embodiments, the humectant may comprise one or more of polyols, including, for example, glycerin, glycerol, glycols, such as, caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers, such as, monopropylene, dipropylene and tripropylene glycol alkyl(C1-C4)ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In accordance with the various embodiments, the amount of humectant or conditioning agent present in the sulfate-free cleansing composition can range from about 1% to about 10%, or from about 1% to about 8%, or from about 1% to about 5%, or from about 2% to about 3%, or any suitable combination, sub-combination, range, or sub-range thereof by weight, based on the weight of the sulfate-free cleansing composition. One of ordinary skill in the art, however, will appreciate that other ranges are within the scope of the invention. One of ordinary skill in the art, however, will appreciate that other ranges are within the scope of the invention.

Thus, any one of or a combination of humectant, when present, may be present, by weight, based on the total weight of the sulfate-free cleansing composition, is from about 1, 2, 3, 4, 5, 6, 7, 8, 9, to about 10 weight percent, including increments and ranges therein and there between.

Preservatives

In accordance with the disclosure, one or more preservatives and/or antimicrobials may be present in the sulfate-free cleansing composition. Any preservative commonly used in cosmetic cleansing compositions is an acceptable preservative for the cleansing compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorphenesin, or salicylic acid, for example. At more concentrated amounts of suitable solvents for optional additives, in particular, suitable solvents for antimicrobials and preservatives, members from the paraben family may be used as a preservative.

In some embodiments, the preservative may comprise one or more of preservatives selected from the group consisting of organic acids, parabens, formaldehyde donors, phenol derivatives, quaternary ammoniums, alcohols, isothiazolinones, and combinations thereof. Preservatives having antibacterial activity are optionally present in the cleansing compositions of the present invention. Examples of organic acid preservatives include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate. Examples of paraben preservatives include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Examples of formaldehyde donor preservatives include, but are not limited to, 1,3-Dimethylol-5,5-dimethylhydantoin (DMDM hydantoin), imidazolidinyl urea, gluteraldehyde, and combinations thereof. Examples of quaternary ammonium preservatives include, but are not limited to, benzalkonium chloride, methene ammonium chloride, benzethonium chloride, and combinations thereof. Examples of alcohol preservatives include, but are not limited to, ethanol, benzyl alcohol, dichlorobenzyl alcohol, phenoxyethanol, and combinations thereof. Examples of isothiazolone preservatives include, but are not limited to, methylchloroisothiazolinone, methylisothiazolinone, and combinations thereof.

In some particular embodiments, appropriate preservatives include, but are not limited to, phenoxyethanol, Tetrasodium EDTA, Zinc Gluconate, Hydroxyacetophenone, Caprylyl glycol, Chlorphenesin, or combinations thereof.

In some embodiments, the preservative includes one or more preservatives, the one or combination present at a concentration, by weight of about 0.001% to about 5%, or alternatively about 0.05% to about 2.5% or alternatively about 0.1% to about 2.0%, based upon weight of the sulfate-free cleansing composition. One of ordinary skill in the art, however, will appreciate that other ranges are within the scope of the invention.

Thus, any one of or a combination of preservatives, when present, may be present, by weight, based on the total weight of the sulfate-free cleansing composition, is from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2, 3, 4, to about 5 weight percent, including increments and ranges therein and there between.

EXAMPLES

The following examples are intended to further illustrate the present disclosure. They are not intended to limit the disclosure in any way. Unless otherwise indicated, all parts are by weight.

Example 1: Inventive Compositions

Exemplary embodiments of the sulfate-free cleansing composition according to the disclosure are set forth in Table 1, below. Notably, Inventive 5 as shown in the table includes a sulfate containing surfactant, and is thus, not properly "sulfate-free."

TABLE 1

Inventive Compositions 1-6

| INGREDIENT | INV 1 | INV 2 | INV 3 | INV 4 | INV 5 | INV 6 |
|---|---|---|---|---|---|---|
| SALICYLIC ACID | 1.20 | 1.20 | 2.0 | 2.0 | 2.0 | 1.2 |
| PEG-60 HYDROGENATED CASTOR OIL | | | | 0.75 | | 0.75 |
| PEG-7 GLYCERYL COCOATE | 0.75 | 0.75 | 0.75 | | 0.75 | |
| PEG-150 PENTAERYTHRITYL TETRASTEARATE | 1.50 | 1.50 | 1.50 | 1.50 | 1.5 | 1.5 |
| SODIUM LAURETH SULFATE | | | | | 30.0 | |
| SODIUM LAUROYL SARCOSINATE | 30.0 | | 11.0 | 11.0 | | 5.0 |
| DISODIUM LAURETH SULFOSUCCINATE (AND) SODIUM LAURYL SULFOACETATE | | | 10.0 | 10.0 | | 18.0 |
| COCAMIDOPROPYL BETAINE | | 30.0 | 5.0 | 5.0 | | 6.0 |
| ADJUSTERS/ADDITIVES (TETRASODIUM GLUTAMATE DIACETATE, ZINC PCA, KOH) | ~2.8 | ~2.8 | ~2.8 | ~2.8 | ~2.8 | ~2.8 |
| ACTIVES (LACTIC ACID, PANTHENOL, TOCOPHERYL ACETATE, ALLANTOIN) | ~2.75 | ~2.75 | ~2.75 | ~2.75 | ~2.75 | ~2.75 |
| HUMECTANT/SOLVENT (SORBITOL, DIPROPYLENE GLYCOL, GLYCERIN) | ~11.5 | ~11.5 | ~11.5 | ~11.5 | ~11.5 | ~11.5 |
| CETYLPYRIDINIUM CHLORIDE, PHENOXYETHANOL, MENTHOL | ~0.8 | ~0.8 | ~0.8 | ~0.8 | ~0.8 | ~0.8 |
| ADDITIVES (FRAGRANCE, PIGMENT) | ~0.20 | ~0.20 | ~0.20 | ~0.20 | ~0.20 | ~0.20 |
| AQUA | ~48 | ~48 | ~50 | ~50 | ~42 | ~44 |

Example 2: Comparative Compositions

Comparative Compositions are shown below in Tables 2 and 3.

TABLE 2

Comparative Compositions (BASED ON INVENTIVE base components, but lacking one or more of the surfactant and solubilizer, and/or including sulfate):

| FORMULATION | SURFACTANT | SOLUBILIZER | Formula Clarity |
|---|---|---|---|
| COMP 1 | 30% SODIUM LAURETH SULFOSUCCINATE (and) SODIUM LAURYL SULFOACETATE | PEG-7 GLYCERYL COCOATE | 100% Clear |
| COMP 2 | 30% Sodium Stearoyl Glutamate | PEG-7 GLYCERYL COCOATE | Haze |
| COMP 3 | 30% SODIUM COCOYL GLYCINATE | PEG-7 GLYCERYL COCOATE | Haze |
| COMP 4 | 30% DECYL GLUCOSIDE (APGs) | PEG-7 GLYCERYL COCOATE | Haze |

TABLE 2-continued

Comparative Compositions (BASED ON INVENTIVE base components, but lacking one or more of the surfactant and solubilizer, and/or including sulfate):

| FORMULATION | SURFACTANT | SOLUBILIZER | Formula Clarity |
|---|---|---|---|
| COMP 5 | 10% SODIUM LAURETH SULFOSUCCINATE (and) SODIUM LAURYL SULFOACETATE 10% Sodium Lauroyl Sarcosinate 6% COCAMIDOPROPYL BETAINE | Polysorbate 20 | 100% Clear initial then turn to Haze after 1-3 weeks |
| COMP 6 | 10% SODIUM LAURETH SULFOSUCCINATE (and) SODIUM LAURYL SULFOACETATE 10% Sodium Lauroyl Sarcosinate 6% COCAMIDOPROPYL BETAINE | OLETH-5 | Haze |
| COMP 7 | 10% SODIUM LAURETH SULFOSUCCINATE (and) SODIUM LAURYL SULFOACETATE 10% Sodium Lauroyl Sarcosinate 6% COCAMIDOPROPYL BETAINE | LAURETH-9 | Haze |
| COMP 8 | 10% SODIUM LAURETH SULFOSUCCINATE (and) SODIUM LAURYL SULFOACETATE 10% Sodium Lauroyl Sarcosinate 6% COCAMIDOPROPYL BETAINE | STEARETH-20 | Haze |

TABLE 3

Benchmark Comparative, sulfate surfactant containing cleanser that lacks the composition of the invention.

| Ingredients | Concentration (% Active) |
|---|---|
| Amphoteric Surfactants (Coco Betaine) | 2.1 |
| Nonionic surfactants (Decyl Glucoside, Peg-150 Pentaerythrityl Tetrastearate (and) Peg-6 Caprylic/Capric Glycerides) | 4.3 |
| Anionic surfactants (Sodium Laureth Sulfate) | 10.14 |
| Conditioning agents - Moisturizer (Glycerin) | 3 |
| Preservatives (Tetrasodium EDTA, Zinc Gluconate) | 0.37 |
| pH adjuster, Salts (Sodium Hydroxide, Citric acid) | 0.47 |
| Actives (Salicylic Acid, Caproyloyl Salicylic Acid) | 2.05 |
| Viscosity Adjuster (Sodium chloride, Hexylene Glycol) | 1 |
| Cooling Agent (Menthol) | 0.1 |
| Water | q.s. to 80 |

Example 3: Demonstration of Effect of Surfactant on Stability

Stability and Haze test results are shown below in Table 4.

In short, each of the listed formulations, including comparative and inventive compositions, were evaluated for clarity (haze) and stability, wherein the surfactant was varied among the tested formulations. Each formulation comprised a Base formulation including 1.2% salicylic acid, PEG-7 glyceryl cocoate, and 30% of the identified anionic surfactant.

TABLE 4

Demonstration of effect of surfactant.

| COMPOSITION | 30% ANIONIC SURFACTANT | HLB VALUE | FORMULA CLARITY | STABILITY (2 MONTH) |
|---|---|---|---|---|
| INV 5 | SODIUM LAURYL SULFATE | 40.1 | 100% Clear | passed |
| INV 1 | SODIUM LAUROYL SARCOSINATE | 29.8 | 100% Clear | passed |
| INV 2 | COCAMIDOPROPYL BETAINE | 35 | 100% Clear | passed |
| COMP 1 | SODIUM LAURETH SULFOSUCCINATE (AND) SODIUM LAURYL SULFOACETATE | 38 | 100% Clear | passed |
| COMP 2 | SODIUM STEAROYL GLUTAMATE | 21.3 | Haze | Phase Separated |
| COMP 3 | SODIUM COCOYL GLYCINATE | 14 | Haze | Phase Separated |

TABLE 4-continued

Demonstration of effect of surfactant.

| COMPOSITION | 30% ANIONIC SURFACTANT | HLB VALUE | FORMULA CLARITY | STABILITY (2 MONTH) |
|---|---|---|---|---|
| COMP 4 | DECYL GLUCOSIDE (APGS) ps: HLB VALUES need >25 | 13 | Haze | Phase Separated |

As shown in the above data, only the inventive formulations that included surfactants selected according to the invention and having an HLB at or greater than 25 demonstrated phase stability, and clarity (lack of haze), the latter being posited to represent maintained solubilization of the salicylic acid. Comparative formulations that did not include surfactant having an HLB at or greater than 25 were hazy (demonstrating non-solvated salicylic acid) and demonstrated phase instability.

Example 4: Demonstration of Effect of Solubilizer on Stability

Stability and Haze test results are shown below in Table 5.

In short, each of the listed formulations, including comparative and inventive compositions, were evaluated for clarity (haze) and stability, wherein the solubilizer was varied among the tested formulations. Each formulation comprised a Base formulation including 2% salicylic acid, 10% Sodium Laureth Sulfosuccinate (and) Sodium Lauryl Sulfoacetate, 10% Sodium Lauroyl Sarcosinate, 6% Cocamidopropyl Betaine, and 0.75% of the identified solubilizer.

TABLE 5

Demonstration of effect of solubilizer

| FORMULATION | SOLUBILIZER | FORMULA CLARITY | STABILITY (2 MONTH) |
|---|---|---|---|
| INV 3 | PEG-7 GLYCERYL COCOATE | 100% Clear | passed |
| INV 4 | PEG-60 HYDROGENATED CASTOR OIL | 100% Clear | passed |
| COMP 5 | Polysorbate 20 | Haze | Phase Separated |
| COMP 6 | OLETH-5 | Haze | Phase Separated |
| COMP 7 | LAURETH-9 | Haze | Phase Separated |
| COMP 8 | STEARETH-20 | Haze | Phase Separated |

As shown in the above data, only the inventive formulations that included solubilizers (PEG containing) selected according to the invention demonstrated phase stability, and clarity (lack of haze). Comparative formulations that did not include PEG based solubilizers were hazy (demonstrating non-solvated salicylic acid) and demonstrated phase instability.

Example 5. Demonstration of Salicylic Acid Deposition of Inventive Composition as Compared to Benchmark (Includes Sulfate Surfactant)

Compositions were evaluated for demonstration of salicylic acid deposition on a synthetic skin material after application of the various tested compositions. The test set up is shown below.

Salicylic Acid Deposition Test

Processing of BIOSKIN Samples: BIOSKIN samples of about 2 in by 2 inches were provided. Each bioskin sample was treated with one of an inventive or comparative composition by application of about 0.5 g of the tested composition with a cleansing brush (Clarisonic™ brush). Cleansed samples were soaked in 40° C. water for about 30 seconds, then massaged using the cleansing brush for about one minute. The samples were then rinsed under water at 40° C. then air dried for about an hour. Samples were then soaked in a solution of iron chloride (0.01% $FeCl_3$) for about an hour then air dried overnight.

The color of each sample of treated BIOSKIN (vs a control sample lacking any treatment) was measured using a hand-held colorimeter and the measurements were analyzed to provide a color change (resulting from binding to the iron compound to deposited SA) reflected as a percentage change in color relative to the control. The results with Bioskin are shown Table 6 and haze test results are shown in Tables 6 and 7.

TABLE 6

Salicylic Acid Deposition and Haze with Inventive, Benchmark and (containing sulfate-based surfactant) and INV base formulation without solublizer.

| | Benchmark Comparative Sulfate-based Surfactant | INV 6 Free of sulfate-based surfactant w/ solubilizer | INVENTIVE Base without solublizer and surfactants No solubilizer & No High HLB Surfactants |
|---|---|---|---|
| % Salicylic Acid | 2% | 1.2% | |
| % Change Average | 15.65 | 18.4 | 7.2 |
| | 100% clear | 100% clear | Hazy |

TABLE 7

Evaluation of Haze with Inventive, Benchmark (containing sulfate-based surfactant) and INV base formulation without solublizer.

| Benchmark | INV 6 | Bright & Clear souffle gel |
|---|---|---|
| 2.0% salicylic acid | 1.2% salicylic acid | 1.2% salicylic acid |
| 100% Clear Gel | 100% Clear Gel | Haze Gel |
| 39% SODIUM LAURETH SULFATE 6% DECYL GLUCOSIDE | 10% SODIUM LAURETH SULFOSUCCINATE (and) SODIUM LAURYL SULFOACETATE | 4.5% SODIUM COCOAMPHOACETATE 4% COCAMIDOPROPYL BETAINE |
| 7% COCO-BETAINE | 10% Sodium Lauroyl Sarcosinate | 4% DISODIUM COCOYL GLUTAMATE (and) SODIUM COCOYL ISETHIONATEBETAINE |
| | 6% COCAMIDOPROPYL BETAINE PEG-150 PENTAERYTHRITYL TETRASTEARATE, PEG-60 HYDROGENATED CASTOR OIL (PEG containing Solubilizers) | |

The data shown above demonstrate that inclusion of the inventive combination of high HLB surfactant and solubilizer promoted post-rinse salicylic acid deposition for the Inventive Composition in a manner comparable to the sulfate containing Benchmark Comparative composition, and significantly outperformed the comparative that includes high HLB surfactants without any solubilizer. Referring to Table 6, the data show that the composition according to the invention with 40% less amount of the salicylic acid than the benchmark achieved similar deposition whilst the comparative compositions based on the inventive formulation but lacking solubilizer did not perform well in deposition and formed a hazy composition, as shown in Tables 6 and 7.

While these results are obtained with the specifically exemplified surfactants and solubilizer, the invention includes other embodiments thereof according to the disclosure that would be contemplated to provide the same or comparable deposition of salicylic acid.

While the disclosure has been described with reference to described embodiments, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one" or "one or more" as used herein, means that there may be one, two, three or more and thus includes individual components as well as mixtures/combinations.

The transitional terms "comprising," "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step, or material. The term "consisting of" excludes any element, step, or material other than those specified in the claim, and, in the latter instance, impurities ordinarily associated with the specified material(s). The term "consisting essentially of" limits the scope of a claim to the specified elements, steps, or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the sulfate-free cleansing composition, typically 0% by weight, based on the total weight of the sulfate-free cleansing composition. The term "essentially free" means that, while it prefers that no excluded material is present in the sulfate-free cleansing composition, it is possible to have very small amounts of the excluded material in the sulfate-free cleansing composition of the invention, provided that these amounts do not materially affect the advantageous properties of the sulfate-free cleansing composition. In particular, "essentially free" means that excluded material can be present in the sulfate-free cleansing composition at an amount of less than about 0.1% by weight, based on the total weight of the sulfate-free cleansing composition.

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., may be modified by the term "about." Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated. As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc. As used herein a range of ratios is meant to include every specific ratio within, and combination of subranges between the given ranges.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:
1. A sulfate-free cleansing composition comprising:
 (a) at least one acne treatment active comprising salicylic acid or a derivative thereof, wherein the salicylic acid or derivative thereof, wherein the salicylic acid or derivative thereof is present in a range from about 1.2% to about 2%, by weight, based on the weight of the sulfate-free cleansing composition; and
 (b) an aqueous carrier comprising:
  i. a combination of surfactants that comprises a sarcosinate surfactant that comprises sodium lauroyl sarcosinate, a betaine surfactant that comprises cocamidopropyl betaine, and at least one other surfactant that is not a sarcosinate surfactant or a betaine surfactant, wherein the at least one other surfactant comprises disodium laureth sulfosuccinate (and) sodium lauryl sulfoacetate,
   wherein each of the surfactants in the combination is present from 1% to about 10%, and wherein the surfactants are present in a total amount of surfactant that is not greater than 20%, by weight, based on the weight of the sulfate-free cleansing composition;
  ii. at least one solubilizer comprising a polyethylene glycol compound that excludes PEG-7 glyceryl cocoate, the polyethylene glycol compound present from about 0.2% to about 2%, by weight, based on the weight of the sulfate-free cleansing composition; and
  iii. water;
 wherein the sulfate-free cleansing composition is essentially free from sulfate-containing compounds and from polyquaternium cationic polymers, and wherein the sulfate-free cleansing composition, when applied to a keratinous tissue, demonstrates deposition and retention of the salicylic acid or derivative thereof on the keratinous tissue after rinsing with water, and wherein the sulfate-free cleansing composition exhibits high foaming and demonstrates stability from phase separation and remains free from hazing at an ambient temperature of about 45° C. for a period of at least 2 months.

2. The sulfate-free cleansing composition according to claim 1, wherein salicylic acid is present in an amount that is about 1.2%, by weight, based on the weight of the sulfate-free cleansing composition.

3. The sulfate-free cleansing composition according to claim 1, wherein salicylic acid is present in an amount that is about 2%, by weight, based on the weight of the sulfate-free cleansing composition.

4. The sulfate-free cleansing composition according to claim 1, wherein the sarcosinate surfactant consists of sodium lauroyl sarcosinate, and the betaine surfactant consists of cocamidopropyl betaine.

5. The sulfate-free cleansing composition according to claim 1, wherein the sarcosinate surfactant consists of sodium lauroyl sarcosinate, and the betaine surfactant consists of cocamidopropyl betaine, and the sulfate-free cleansing composition includes one or more additives selected from the group consisting of water-based solvents, humectants, pH adjusters, chelating agents, skin care actives, preservatives, fillers, fragrances, dyes, pigments, and combinations thereof.

6. The sulfate-free cleansing composition according to claim 1, wherein the at least one solubilizer comprising a polyethylene glycol compound is present in an amount that is about 1.5%, by weight, based on the weight of the sulfate-free cleansing composition.

7. The sulfate-free cleansing composition according to claim 1 wherein the at least one other surfactant that is not a sarcosinate surfactant or a betaine surfactant includes a surfactant selected from the group consisting of Disodium Laureth Sulfosuccinate, Disodium Lauryl Sulfosuccinate, Diethylhexyl Sodium Sulfosuccinate, Disodium Laureth Sulfosuccinate, Sodium Lauryl Sulfoacetate, and combinations thereof.

8. The sulfate-free cleansing composition according to claim 1, wherein the at least one solubilizer comprising a polyethylene glycol compound is selected from the group consisting of PEG-60 hydrogenated castor oil, PEG-150 pentaerythrityl tetrastearate, PEG-40 Hydrogenated Castor Oil, PEG-80 Hydrogenated Castor Oil, PEG-30 Glyceryl Cocoate, PEG-80 Glyceryl Cocoate, and combinations thereof.

9. A sulfate-free cleansing composition comprising:
 (a) at least one acne treatment active comprising salicylic acid or a derivative thereof, wherein the salicylic acid or derivative thereof, wherein the salicylic acid or derivative thereof is present in a range from about 1.2% to about 2%, by weight, based on the weight of the sulfate-free cleansing composition; and (b) an aqueous carrier comprising:
  i. a combination of surfactants that comprises a sarcosinate surfactant that comprises sodium lauroyl sarcosinate, a betaine surfactant that comprises cocamidopropyl betaine, and at least one other surfactant that is not a sarcosinate surfactant or a betaine surfactant, wherein the at least one other surfactant comprises disodium laureth sulfosuccinate (and) sodium lauryl sulfoacetate,
    wherein each of the surfactants in the combination is present from 1% to about 10%, and wherein the surfactants are present in a total amount of surfactant that is not greater than 20%, by weight, based on the weight of the sulfate-free cleansing composition;
  ii. at least one solubilizer comprising a polyethylene glycol compound that excludes PEG-7 glyceryl cocoate, the polyethylene glycol compound present from about 0.2% to about 2%, by weight, based on the weight of the sulfate-free cleansing composition; and
  iii. water;
wherein the sulfate-free cleansing composition is essentially free from sulfate contents and from polyquaternium cationic polymers, and wherein the sulfate-free cleansing composition, when applied to a keratinous tissue, demonstrates deposition and retention of the salicylic acid or derivative thereof on the keratinous tissue after rinsing with water, and wherein the sulfate free cleansing composition exhibits high foaming and demonstrates stability from phase separation and remains free from hazing at an ambient temperature of about 45° C. for a period of at least 2 months, and wherein the sulfate-free cleansing composition is free of cationic compounds and sulfate-based surfactants.

10. The sulfate-free cleansing composition according to claim 1, wherein the sulfate-free cleansing composition is free from sulfate-containing compounds.

11. The sulfate-free cleansing composition according to claim 1, further comprising one or more additives selected from the group consisting of water-based solvents, humectants, pH adjusters, chelating agents, skin care actives, preservatives, fillers, fragrances, dyes, pigments, and combinations thereof.

12. The sulfate-free cleansing composition according to claim 1, further comprising one or more additives selected from the group consisting of allantoin, potassium hydroxide, dyes, pigments, dipropylene glycol, panthenol, phenoxyethanol, menthol, tocopheryl acetate, glycerin, lactic acid, fragrance, zinc PCA, tetrasodium glutamate diacetate, sorbitol, cetylpyridinium chloride, and combinations thereof.

13. A sulfate-free cleansing composition comprising:
(a) at least one acne treatment active comprising salicylic acid or a derivative thereof, wherein the salicylic acid or derivative thereof, wherein the salicylic acid or derivative thereof is present in a range from about 1.2% to about 2%, by weight, based on the weight of the sulfate-free cleansing composition; and
(b) an aqueous carrier comprising:
  i. a combination of surfactants that comprises a sarcosinate surfactant that comprises sodium lauroyl sarcosinate, a betaine surfactant that comprises cocamidopropyl betaine, and at least one other surfactant that is not a sarcosinate surfactant or a betaine surfactant, wherein the at least one other surfactant comprises disodium laureth sulfosuccinate (and) sodium lauryl sulfoacetate,
    wherein each of the surfactants in the combination is present from 1% to about 10%, and wherein the surfactants are present in a total amount of surfactant that is not greater than 20%, by weight, based on the weight of the sulfate-free cleansing composition;
  ii. at least one solubilizer comprising a polyethylene glycol compound present from about 0.2% to about 2%, by weight, based on the weight of the sulfate-free cleansing composition, and excluding PEG-7 glyceryl cocoate;
  iii. water, and
  iv. one or more additives selected from the group consisting of water-based solvents, humectants, pH adjusters, chelating agents, skin care actives, preservatives, fillers, fragrances, dyes, pigments, and combinations thereof
wherein the sulfate-free cleansing composition is free or essentially free from sulfate contents and from quaternary ammoniums other than betaines.

14. The sulfate-free cleansing composition according to claim 13, wherein salicylic acid is present in an amount that is about 1.2%, by weight, based on the weight of the sulfate-free cleansing composition.

15. The sulfate-free cleansing composition according to claim 13, wherein salicylic acid is present in an amount that is about 2%, by weight, based on the weight of the sulfate-free cleansing composition.

16. The sulfate-free cleansing composition according to claim 1 wherein the at least one other surfactant that is not a sarcosinate surfactant or a betaine surfactant includes a surfactant selected from the group consisting of Disodium Laureth Sulfosuccinate, Disodium Lauryl Sulfosuccinate, Diethylhexyl Sodium Sulfosuccinate, Disodium Laureth Sulfosuccinate, Sodium Lauryl Sulfoacetate, and combinations thereof.

17. The sulfate-free cleansing composition according to claim 1, wherein the at least one solubilizer comprising a polyethylene glycol compound is selected from the group consisting of PEG-60 hydrogenated castor oil, PEG-150 pentaerythrityl tetrastearate, PEG-40 Hydrogenated Castor Oil, PEG-80 Hydrogenated Castor Oil, PEG-30 Glyceryl Cocoate, PEG-80 Glyceryl Cocoate, and combinations thereof.

18. The sulfate-free cleansing composition according to claim 1, further comprising one or more additives selected from the group consisting of allantoin, potassium hydroxide, dyes, pigments, dipropylene glycol, panthenol, phenoxyethanol, menthol, tocopheryl acetate, glycerin, lactic acid, fragrance, zinc PCA, tetrasodium glutamate diacetate, sorbitol, cetylpyridinium chloride, and combinations thereof.

19. The sulfate-free cleansing composition according to claim 1 wherein the sulfate-free cleansing composition includes less than 0.1% by weight of the sulfate-containing compounds.

20. The sulfate-free cleansing composition according to claim 1 wherein the sulfate-free cleansing composition includes less that 0.2% by weight of sulfate-based surfactant.

\* \* \* \* \*